(12) United States Patent
Morishita et al.

(10) Patent No.: US 6,248,722 B1
(45) Date of Patent: *Jun. 19, 2001

(54) MEDICAMENT COMPRISING HGF GENE

(75) Inventors: Ryuichi Morishita, Osaka; Toshio Ogihara, Mino; Toshikazu Nakamura, Takatsuki; Tetsuya Tomita, Toyonaka; Takahiro Ochi, Kobe, all of (JP)

(73) Assignee: Sumitomo Pharmaceuticals Company, Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,497

(22) PCT Filed: Aug. 22, 1996

(86) PCT No.: PCT/JP96/02359

§ 371 Date: Jun. 9, 1998

§ 102(e) Date: Jun. 9, 1998

(87) PCT Pub. No.: WO97/07824

PCT Pub. Date: Jun. 3, 1997

(30) Foreign Application Priority Data

Aug. 29, 1995 (JP) .................................................. 7-245475
Feb. 20, 1996 (JP) .................................................. 8-058467

(51) Int. Cl.$^7$ ........................ A61K 31/711; A61K 9/127
(52) U.S. Cl. ........................................... 514/44; 424/450
(58) Field of Search ............................. 424/450; 514/44; 536/23.1, 23.5, 23.51

(56) References Cited

U.S. PATENT DOCUMENTS 5,652,225 * 7/1997 Isner ........................................ 514/44
5,756,122 * 5/1998 Thierry et al. ....................... 424/450

FOREIGN PATENT DOCUMENTS

| 0461560 | 12/1991 | (EP) . |
| 0492614 | 7/1992 | (EP) . |
| 0494369 | 7/1992 | (EP) . |
| WO 91/06309 | 5/1991 | (WO) . |
| WO9205184 | 4/1992 | (WO) . |
| WO9308821 | 5/1993 | (WO) . |
| WO9406456 | 3/1994 | (WO) . |
| WO 96/40062 | 12/1996 | (WO) . |

OTHER PUBLICATIONS

"Scatter Factor (Hepatocyte Growth Factor) is a Potent Angiogenesis Factor In Vivo" by Rosen et al., Society of Experimental Biology 1993, pp. 227–234.

"Scatter Factor Induces Blood Vessel Formation In Vivo" by Grant et al., Proc. Natl. Acad. Sci. USA, vol. 90, Mar. 1993, pp. 1937–1941.

"Hepatocyte Growth Factor/Scatter Factor Modulates Cell Motility, Proliferation, and Proteoglycan Synthesis of Chondrocytes" by Takebayashi et al., Journal of Cell Biology, vol. 129, No. 5, Jun. 1995, pp. 1411–1419 EXS.

"The Interaction of HGF–SF with Other Cytokines in Tumor Invasion and Angiogensis" by Rosen et al., vol. 65, 1993, pp. 301–310.

Gut, Supplement No. 5, vol. 35, s–60, F240 (1994), Selden et al.

Biochem. and Biophys. Res. Comm., 220, 539–545 (1996), Hayashi et al, "Autocrine–Paracrine Effects of Overexpression of Hepatocyte Growth Factor Gene on Growth of Endothelial Cells".

Verma et al. Sep. (1997) Gene therapy–promises, problems and prospects. Nature 389:239–242.*

Morishita et al. Jun. (1993) Novel in vitro gene transfer method for study of local modulators in vascular smooth muscle cells. Hypertension 21:894–899.*

Nakamura et al., "Molecular Cloning and Expression of Human Hepatocyte Growth Factor", Nature, Vol. 342, Nov. 23, 1989, Pgs. 440–443, XP000652120.

Miyazawa K. et al., "Molecular Cloning and Sequence Analysis of cDNA for Human Hepatocyte Growth Factor" Biochemical and Biophysical Research Communications, Vol. 163, No. 2, Set. 15, 1989, Pgs. 967–973, XP000651424.

T. Seki et al., "Isolation and Expression of cDNA for Differnt Forms of Hepatocyte Growth Factor" Biochemical and Biophysical Research Communications, Vol. 172, No. 1, Oct. 15, 1990, Pgs. 321–327, XP002084490.

* cited by examiner

Primary Examiner—Robert A. Schwartzman
(74) Attorney, Agent, or Firm—Sughrue, Mion, Zinn, Macpeak & Seas, PLLC (57) ABSTRACT

The present invention relates to a medicament comprising a HGF gene. The medicament of the present invention may be topically applied to the target organs so that the effects can be selectively exhibited, resulting in minimizing the side effects of HGF.

6 Claims, 10 Drawing Sheets

MEDICAMENT COMPRISING HGF GENE

TECHNICAL FIELD TO WHICH THE INVENTION PERTAINS

The present invention relates to a medicament for use in the gene therapy and the like. More particularly, the present invention relates to a medicament comprising a hepatocyte growth factor (HGF) gene as well as a liposome containing the HGF gene.

PRIOR ARTS

HGF is a physiologically active peptide that exhibit diverse pharmacological activities. The pharmacological activities of HGF are described in, e.g., JIKKEN-IGAKU (Experimental Medicine), Vol. 10, No. 3 (extra issue), 330–339 (1992). In view of its pharmacological activities, HGF is expected to be useful as a drug for the treatment of liver cirrhosis or renal diseases; epithalial cell growth accelerators; anti-cancer agents; agents for the prevention of side effects in cancer therapy; agents for the treatment of lung disorders, gastrointestinal damages or cranial nerve disorders; agents for the prevention of side effects in immunosuppression; collagen degradation accelerators; agents for the treatment of cartilage disorders, arterial diseases, pulmonary fibrosis, hepatic diseases, blood coagulopathy, plasma hypoproteinosis or wounds; agents for the improvement of nervous disorders; hematopoietic stem cell potentiators; and hair growth promoters (Japanese Patent KOKAI (Laid-Open) Nos. 4-18028 and 4-49246, EP 492614, Japanese Patent KOKAI (Laid-Open) No. 6-25010, WO 93/8821, Japanese Patent KOKAI (Laid-Open) Nos. 6-172207, 7-89869 and 6-40934, WO 94/2165, Japanese Patent KOKAI (Laid-Open) Nos. 6-40935, 6-56692 and 7-41429, WO 93/3061, Japanese Patent KOKAI (Laid-Open) No. 5-213721, etc.).

As to gene therapy, extensive studies and investigations have been currently made all over the world for adenosine deaminase deficiency, AIDS, cancer, pustulous fibrosis or hemophilia, etc.

However, gene therapy using the HGF genes is unknown yet. It is even unclear if such gene therapy is effectively applicable.

Problems to be Solved by the Invention

HGF is known to be one of the drugs that have a short half life in blood. As a natural consequence, persistent topical administration has been desired for HGF.

In view of the diverse pharmacological activities of HGF, HGF is expected to be developed as a drug having extended applications to various diseases. On the other hand, when HGF is systemically administered, side effects might be caused due to the diverse pharmacological activities of HGF. In addition, when HGF itself is intravenously administered, HGF encounters such a drawback that a considerable amount of HGF is retained in the liver, resulting in reduction of the amount of HGF to reach the target organ.

Means for Solving the Problems

The present invention has been made to solve the foregoing problems. In summary, the present invention relates to:

(1) a medicament comprising a HGF gene;
(2) a liposome containing the HGF gene;
(3) a liposome according to (2), which is a membrane fusion liposome fused to Sendai virus;
(4) a medicament comprising the liposome according to (2) or (3);
(5) a medicament according to (1) or (4), for use in the treatment for arterial disorders; and,
(6) a medicament according to (1) or (4), for use in the treatment for cartilage injuries.

BEST MODE FOR CARRYING OUT THE INVENTION

The "HGF gene" employed in the present invention indicates a gene capable of expressing HGF. Thus, so long as a polypeptide expressed has substantially the same effect as that of HGF, the HGF gene may have a partial deletion, substitution or insertion of the nucleotide sequence, or may have other nucleotide sequence ligated therewith at the 5'-terminus and/or 3'terminus thereof. Typical examples of such HGF genes include HGF genes as described in Nature, 342, 440 (1989), Japanese Patent KOKAI (Laid-Open) No. 5-111383, Biochem. Biophys. Res. Commun., 163, 967 (1989), etc. These genes may be used in the present invention.

The HGF gene is incorporated into an appropriate vector and the HGF gene-bearing vector is provided for use. For example, the HGF gene may be used in the form of a viral vector having the HGF gene as described hereinafter, or in the form of an appropriate expression vector having the HGF gene.

The "pharmaceutical composition" used in the present invention indicates a medicament for the treatment or prevention of human diseases, which is attributed to the pharmacological activities of HGF. For example, exemplified are medicaments for the treatment or prevention of the diseases given hereinabove.

According to the present invention, the HGF gene is introduced into cells wherein HGF is expressed in those cells to exhibit the pharmacological actions. Thus, the medicament of the present invention is effectively applicable to the diseases for which HGF itself is effective.

Where the HGF gene is introduced into, e.g., cells, the growth of vascular endothelial cells is accelerated, while undesired growth of vascular smooth muscle cells is not accelerated, as demonstrated in the Examples hereinafter. Moreover, as demonstrated in the Example hereinafter, where the HGF gene is introduced into the heart in vivo animal test using rats, angiogenesis is observed. Therefore, the HGF gene is effective for the treatment and prevention of arterial disorders, in particular, various diseases caused by disturbance which mainly involves abnormal proliferation of vascular smooth muscle cells (e.g., restenosis after percutaneous transluminal coronary angioplasty (PTCA), arteriosclerosis, insufficiency of peripheral circulation, etc.), and for the treatment and prevention of diseases such as myocardial infarction, myocardia, peripheral angiostenosis, cardiac insufficiency, etc. HGF itself is also useful for the treatment and prevention of the diseases as described above, since HGF promotes the proliferation of vascular endothelial cells but does not promote the growth of vascular smooth muscle cells. The pharmacological effects of the HGF gene are attributed to those of HGF itself.

As demonstrated in the Examples hereinafter, introduction of the HGF gene into the joint results in promoting repair of articular cartilage cells thereby to promote the proliferation of proteoglycan-synthesizing cells. Therefore, the HGF gene is effective for the prevention and treatment of various cartilage injuries such as osteogenetic abnormality, arthritis deformans, discopathy deformans, fracture repair and restoration insufficiency, trauma caused by sporting, key puncher's disease, etc. HGF itself is useful for the treatment and prevention of the diseases described above, since HGF promotes repair and growth of cartilage cells. The effects of the HGF gene are based on those of HGF itself.

"Liposome" is a closed vesicle of lipid bilayer encapsulating an aqueous compartment therein. It is known that the lipid bilayer membrane structure is extremely similar to biological membranes. To prepare the liposomes of the present invention, phospholipids are employed. Typical examples of phospholipids are phosphatidylcholines such as lecithin, lysolecithin, etc.; acidic phospholipids such as phosphatidylserine, phosphatidylglycerol, phosphatidylinositol, phosphatidylic acid, etc.; or phospholipids obtained by replacing an acyl group(s) of these acidic phospholipids with lauroyl, myristoyl, oleoyl, etc.; and sphingophospholipids such as phosphatidylethanolamine, sphingomyelin, etc. Neutral lipids such as cholesterol may also be added to these phospholipids. The liposomes may be prepared, in a conventional manner, from naturally occurring materials such as lipids in normal cell membranes. The liposomes containing the HGF gene of the present invention may be prepared, for example, by suspending a thin layer of purified phospholipids in a solution containing the HGF gene and then treating the suspension in a conventional manner such as ultrasonication.

The liposomes containing the HGF gene of the present invention may be appropriately fused to viruses, etc. to form membrane fusion liposomes. In this case, it is preferred to inactivate viruses, e.g., through ultraviolet irradiation, etc. A particularly preferred example of the membrane fusion liposome is a membrane fusion liposome fused with Sendai virus (hemagglutinating virus of Japan: HVJ). The membrane fusion liposome may be produced by the methods as described in NIKKEI Science, April, 1994, pages 32–38; J. Biol. Chem., 266 (6), 3361–3364 (1991), etc. In more detail, the HVJ-fused liposome (HVJ-liposome) may be prepared, e.g., by mixing purified HVJ inactivated by ultraviolet irradiation, etc. with a liposome suspension containing the HGF gene vector, gently agitating the mixture and then removing unbound HVJ by sucrose density gradient centrifugation. The liposomes may be bound to substances having an affinity to target cells, thereby to enhance an efficiency of gene introduction into the target cells. Examples of the substances having an affinity to the target cells include ligands such as an antibody, a receptor, etc.

For introduction of the HGF gene into cells, conventional methods are employed, which are roughly classified into introduction via viral vectors and other strategies (NIKKEI Science, April, 1994, pages 20–45; GEKKAN YAKUJI, 36 (1), 23–48 (1994) and references cited therein). Both methods are available for the preparation of the medicament of the present invention.

The former method using viral vectors comprises the step of incorporating the HGF gene into, e.g., a retrovirus, an adenovirus, an adeno-related virus, a herpes virus, a vaccinia virus, a poliovirus, a sindbis virus or other RNA viruses. Of these viruses, a retrovirus, an adenovirus and an adeno-related virus are particularly preferably employed for the introduction.

Examples of the other methods include the liposome method, lipofectin method, microinjection method, calcium phosphate method, electroporation method. Of these methods, particularly preferred is the liposome method.

For practical use of the HGF gene as a medicament, it is advantageous to introduce the HGF directly into the body (in vivo method). Alternatively, certain cells are collected from human, the HGF gene is then introduced into the cells outside the body and the HGF gene-introduced cells are returned to the body (ex vivo method). These methods are described in NIKKEI Science, April, 1994, pages 20–45; GEKKAN-YAKUJI, 36 (1), 23–48 (1994) and references cited therein. Any of these methods are suitably chosen depending upon a disease to be treated, target organs, etc. and applied to the medicament compositions of the present invention.

The in vivo method is less costly, less laborious and therefore more convenient than the ex vivo method, but the latter method provides a higher efficiency of introduction of the HGF gene into cells.

Where the medicament of the present invention is administered by the in vivo method, the medicament may be administered through any route appropriate for diseases to be treated, target organs, etc. The medicament may be administered intravenously, intraarterially, subcutaneously, intramuscularly, etc., or directly to the objective organ of diseases, e.g., kidney, liver, lung, brain, nerve, etc. Direct administration to the objective site can treat the target organ selectively. For example, in gene therapy using a gene for restenosis after PTCA, the composition may be administered intraarterially (JIKKEN-IGAKU, 12 (extra issue 15), 1298–1933 (1994). Preferably, the medicament of the present invention is applied at the tip of a balloon used for PTCA and rubbed the tip against blood vessel, whereby the medicament may be introduced directly into vascular endothelial cells and vascular smooth muscle cells.

Where the ex vivo method as described above is used to introduce the HGF gene, human cells (e.g., lymphocytes or hematopoietic stem cells) are harvested in a conventional manner and the harvested cells are sensitized with the medicament of the present invention for gene introduction. Thereafter the HGF-producing cells are inserted back to human.

Where the medicament is administered by the in vivo method, the medicament may take various preparation forms, including the form of liquid preparation. In general, the medicament may be preferably prepared into an injection comprising the HGF gene as an active ingredient. If necessary and desired, conventional carriers may be added to the composition. The injection may be prepared in a conventional manner, e.g., by dissolving the HGF gene in an appropriate solvent (e.g., sterilized water, a buffered solution, a physiological saline solution, etc.), filtering the solution through a filter, etc. for sterilization, filling up the solution in a sterile container. The medicament may be prepared using the HGF gene-incorporated viral vector, instead of the HGF gene itself. Where the liposomes containing the HGF gene embedded therein (or HVJ-liposomes) are employed, the medicament may be in the form of liposome preparations such as a suspension, a frozen preparation, a centrifugally concentrated frozen preparation, etc.

The content of the HGF gene in the medicament may be appropriately varied depending upon diseases to be treated, target organs, patients' ages or body weights, etc. However, it is appropriate to administer in a dose of 0.0001 mg to 100 mg, preferably 0.001 mg to 10 mg when calculated as the HGF gene. The dose may be divided into several days or a few months.

EXAMPLES

Hereinafter the present invention will be described in more detail with reference to the examples but is not deemed to be limited thereto. Materials and methods used in the following examples are outlined below.

Materials and Methods (1) HGF Expression Vector

The HGF expression vector was prepared by inserting human HGF cDNA (2.2 kb, Biochem. Biophys. Res. Commun., 172, 321–327 (1990); Japanese Patent KOKAI (Laid-Open) No. 5-111383) between the EcoRI and NotI sites of pUC-SRα expression vector (FEBS, 333, 61–66 (1993)). In this plasmid vector, transcription of HGF cDNA is regulated by SRa promoter (Nature, 342, 440–443 (1989)).

(2) Cell Culture

Rat coronary endothelial cells were isolated from the enzymatically digested heart of 8 weeks aged Sprague-Dawley (SD) rats by density gradient centrifugation (Transplantation, 57, 1653–1660 (1994)). Rat aortic vascular smooth muscle cells (VSMCs) were obtained from 12 weeks aged SD rats by enzymatic treatment (J. Clin. Invest., 93, 355–360 (1994)). These cells were maintained in DMEM medium supplemented with 10% (vol/vol) calf fetal serum, penicillin (100 U/ml) and streptomycin (100 μg/ml). The cells were incubated at 37° C. in a humidified 95% air-5% $CO_2$ atmosphere. The culture medium was routinely changed at 2 day-intervals. Both immunopathological and morphological observation revealed that these cells were endothelial cells and smooth muscle cells, respectively.

Human aortic endothelial cells (five passages) and human VSMCs (five passages) were obtained from Kurabo Co. The endothelial cells were incubated in a manner similar to the above method in MCDB131 medium supplemented with 5% calf fetal serum, epidermal growth factor (10 ng/ml), basic fibroblast growth factor (2 ng/ml) and dexamethasone (1 μM).

Endothelial cells in the stationary state were prepared according to the method described in J. Clin. Invest., 86, 1690–1697 (1990), ibid., 94, 824–829 (1994).

(3) Transfection of the HGF Gene into HVJ-liposomes in Vitro

Endothelial cells or VSMCs were inoculated for sensitization on a 6-well plate in a cell count of $10^6$ and proliferated to reach 80% confluence. The cells were washed 3 times with a balanced salt solution (137 mM NaCl, 5.4 mM KCl, 10 mM Tris-HCl, pH 7.6; hereinafter abbreviated as "BSS") supplemented with 2 mM calcium chloride. To the cells was added 1 ml of a solution of the HVJ-liposome-DNA (containing 2.5 mg of lipids and 10 mg of the embedded DNA) obtained in Example 1 hereinafter or 1 ml of a solution of the HVJ-liposome-cont obtained in Comparative Example 1 hereinafter. The resulting mixture was incubated at 4° C. for 5 minutes and at 37° C. for further 30 minutes. The cells were washed and maintained in a fresh medium containing 10% bovine serum in a $CO_2$ incubator.

(4) Assay for the HGF Concentrations in Endothelial Cells and VSMCs

The concentration of HGF produced from the sensitized endothelial cells and VSMCs was assayed by ELISA. That is, rat or human endothelial cells or VSMCs were inoculated on a 6-well plate (made by Corning) in a cell density of $5 \times 10^4$ cells/$cm^2$, followed by incubation for 24 hours. The medium was replenished 24 hours after the sensitization, and incubation was continued for further 48 hours. To investigate if HGF was released, the sensitized cells (48 hours after sensitization) were washed and added to 1 ml of a serum-free medium containing $5 \times 10^{-7}$ M insulin, 5 μg/ml transferrin and 0.2 mM ascorbate. After 24 hours, the culture media were collected, centrifuged at 600 g for 10 minutes and then stored at −20° C.

The HGF concentration in the media was determined by an enzyme immunoassay using an anti-rat HGF antibody or an anti-human HGF antibody (Exp. Cell Res., 210, 326–335 (1994); Jpn. J. Cancer Res., 83, 1262–1266 (1992)). A rabbit anti-rat or an anti-human HGF IgG was coated onto a 96-well plate (made by Corning) at 4° C. for 15 hours. After blocking with 3% bovine serum albumin-containing PBS (phosphate buffered saline), the culture medium was added to each well, and incubation was performed at 25° C. for 2 hours. After washing each well 3 times with PBS containing 0.025% Tween (PBS-Tween), a biotinated rabbit anti-rat HGF IgG or an anti-human HGF IgG was added to each well followed by incubation at 25° C. for 2 hours. After washing with PBS-Tween, each well was incubated together with horse radish peroxidase-bound streptoavidin-biotin complex (PBS-Tween solution). The enzymatic reaction was initiated by adding thereto a substrate solution (containing 2.5 mM o-phenylenediamine, 100 mM sodium phosphate, 50 mM citrate and 0.015% hydrogen peroxide). The reaction was terminated by adding 1 M sulfuric acid to the system. Absorbance was measured at 490 nm. The anti-human HGF antibody is cross-reactive only with human HGF but not with rat HGF. The anti-rat HGF antibody is cross-reactive solely with rat HGF but not with human HGF.

(5) HGF

The human and rat recombinant HGFs employed were purified from the culture solution of CHO cells or C-127 cells transfected with an expression plasmid bearing human or rat HGF cDNA (Cell, 77, 261–271 (1994); J. Clin. Invest., 93, 355–360 (1994)).

(6) Statistical Analysis

All runs were repeated at least 3 times. Data measured are shown by mean±standard error. Statistical analysis of the measured data was made according to the Duncan's test.

(7) Hematoxylin-Eosin (HE) Staining and Azan Staining

Ten days after the gene introduction, the HGF gene-introduced rats were sacrificed by perfusion with heparinized physiological saline. Fixation was then made overnight with a 4% paraformaldehyde PBS solution. After fixation, the tissue was embedded in paraffin. Slides were prepared and stained with HE and Azan in a conventional manner. The slides were examined on a microscope to count the number of microvessels.

EXAMPLE 1

Preparation of HVJ-liposomes Containing the HGF Expression Vector

Phosphatidylserine, phosphatidylcholine and cholesterol were mixed with tetrahydrofuran in a weight ratio of 1:4.8:2. By distilling tetrahydrofuran off through a rotary evaporator, the lipid mixture (10 mg) was precipitated onto the container wall. After 96 μg of high mobility group (HMG) 1 nuclear protein purified from bovine thymus was mixed with a BBS (200 μl) solution of plasmid DNA (300 μg) at 20° C. for an hour, the mixture was added to the lipid mixture obtained above. The resulting liposome-DNA-HMG 1 complex suspension was mixed with a vortex, ultrasonicated for 3 seconds and then agitated for 30 minutes.

The purified HVJ (strain Z) was inactivated by UV irradiation (110 erg/$mm^2$ sec) for 3 minutes immediately before use. BSS was added to and mixed with the liposome suspension (0.5 ml, containing 10 mg of the lipids) obtained above and HVJ (20,000 hemagglutinating units) to make the whole volume 4 ml. The mixture was incubated at 4° C. for 10 minutes and gently agitated at 37° C. for further 30 minutes. The unreacted HVJ was removed from the HVJ-liposomes by sucrose density gradient centrifugation. That is, the upper layers in the sucrose density gradient were collected to give the HVJ-liposomes containing the HGF expression vector (containing 10 μg/ml of the HGF expression vector). The HVJ-liposomes containing the HGF expression vector is hereinafter often referred to as HVJ-liposome-DNA.

EXAMPLE 2

Administration of the HVJ-liposome Containing the HGF Expression Vector to Rats The HVJ-liposomes containing the HGF expression vector were prepared by the method as described in the above Example, using 64 μg of HMG 1 nuclear protein and 200 μg of plasmid DNA. BSS was added to and mixed with the liposome suspension (0.5 ml, containing 10 mg of the lipids) and HVJ (35,000 hemagglutinating units) to make the whole volume 2 ml.

SD rats (weighing 400–500 g; purchased from Japan Charles River) were anesthetized with intraperitoneal administration of sodium pentobarbital (0.1 ml/100 mg), warmed and maintained breathing by an automated breather. The rats were subjected to thoracotomy at the left side. The HVJ-liposome-DNA or HVJ-liposome-cont (20 μl) was carefully injected directly through the cardiac apex using a 30 G syringe.

COMPARATIVE EXAMPLE 1

Preparation of HVJ-liposomes Containing no HGF Expression Vector

A vector bearing no HGF gene was treated in the same manner as described in Example 1 to prepare the HVJ-liposomes containing no HGF expression vector. The HGF expression vector-free HVJ-liposomes are hereinafter referred to as HVJ-liposome-cont.

COMPARATIVE EXAMPLE 2

Preparation of HVJ-liposomes Containing Human TGF-β Expression Vector

HVJ-liposomes containing human TGF-β expression vector were prepared in a manner similar to Example 1 except for using human TGF-β expression vector.

The HVJ-liposomes containing human TGF-expression vector are hereinafter referred to as HVJ-liposome-DNA (TGF-β).

TEST EXAMPLE 1

Expression of HGF in Rat Coronary Endothelial Cells Sensitized with HVJ-liposome-DNA HVJ-liposome-DNA (concentration of the HGF expression vector in liposomes: 10 μg/ml) was sensitized to rat coronary endothelial cells (cell count: $10^6$). HGF production was determined by ELISA. For control, a similar test was conducted using HVJ-liposome-cont. HGF production was also determined on the non-sensitized rat coronary endothelial cells (no-treatment group). The results are shown in FIG. 1 (n=6), wherein "HGF" represents the group of rat coronary endothelial cells sensitized with HVJ-liposome-DNA.

Figure 1:
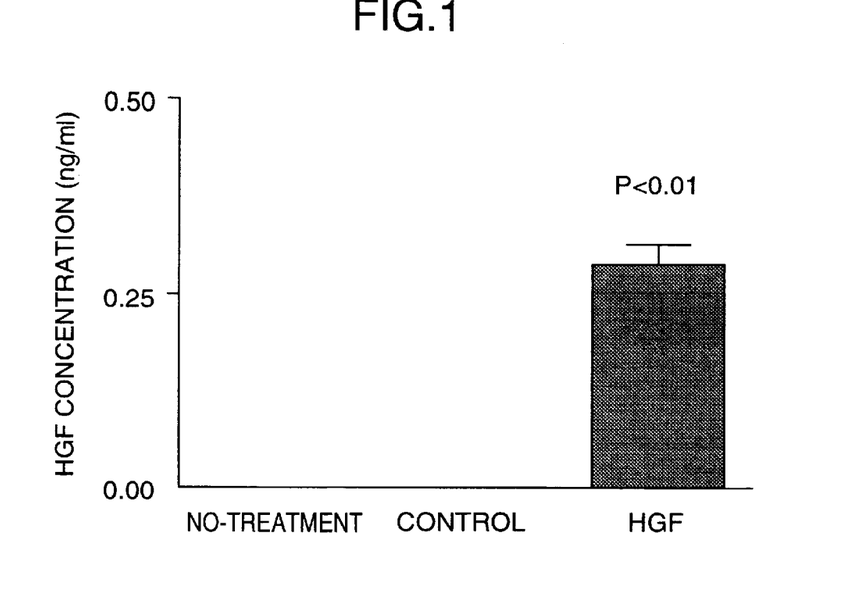
FIG. 1 shows an expression of HGF in rat coronary endothelial cells sensitized with the hemagglutinating virus of Japan (HVJ)-liposome-DNA in Test Example 1.

As shown in FIG. 1, the rat coronary endothelial cells sensitized with HVJ-liposome-DNA produced and secreted HGF on a high level. On the other hand, HGF production was not substantially observed either in the intact group or in the group of the rat coronary endothelial cells sensitized with HVJ-liposome-cont.

Cell counting in the groups tested reveals that the HGF expression group showed significantly high cell counts.

TEST EXAMPLE 2

Figure 2:
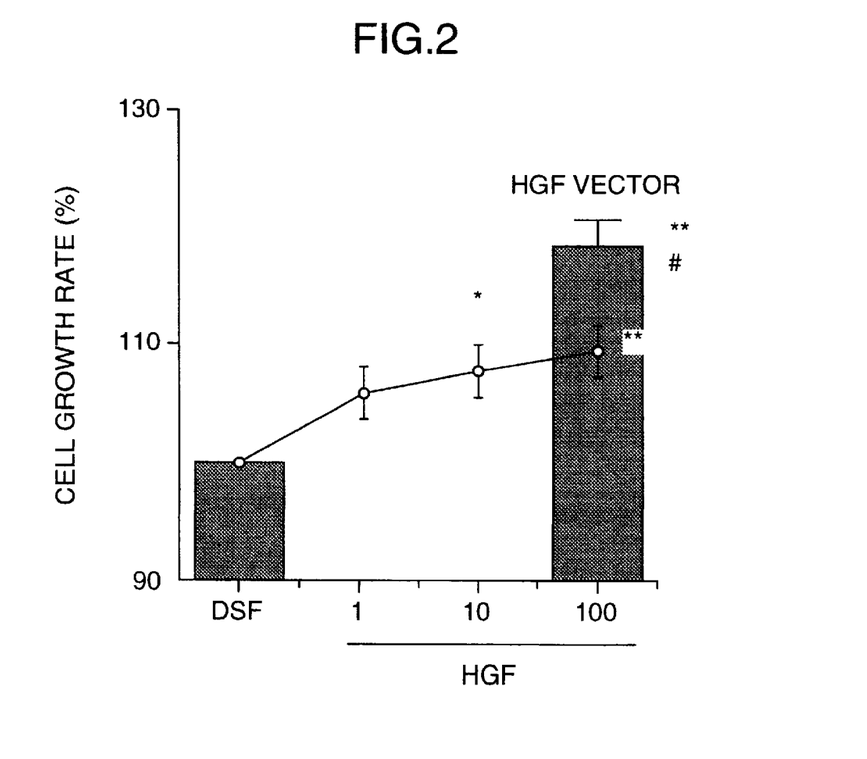
In FIG. 2, the (line) graph shows a cell growth rate in the presence or absence of HGF from the HVJ-liposome-cont-sensitized endothelial cells in Test Example 2, wherein "DSF" designates a group of the endothelial cells sensitized with HVJ-liposome-cont and "HGF" designates a group incubated in the presence of recombinant human HGF in a predetermined concentration. The bar in FIG. 2 shows a cell growth rate of the HVJ-liposome-DNA-sensitized endothelial cells in Test Example 2, wherein "DSF" designates a group of the endothelial cells sensitized with HVJ-liposome-cont and "HGF vector" designates a group of the endothelial cells sensitized with HVJ-liposome-DNA.

Effects of the Sensitized HGF Expression Vector on Proliferation of Endothelial Cells Human endothelial cells were sensitized with HVJ-liposome-cont. The sensitized cells were incubated in the presence or absence of added exogenously recombinant human HGF (1, 10 and 100 ng/ml) and a cell growth rate (%) was determined. The results are shown in FIG. 2 ((line) graph, n=6), wherein "DSF" represents the group of the endothelial cells sensitized with HVJ-liposome-cont and "HGF" represents shows the group incubated in the presence of recombinant human HGF in a definite concentration (*: P<0.05, **: P<0.01 for DSF).

The (line) graph shown in FIG. 2 reveals that the growth of endothelial cells is promoted by the exogenously added HGF.

The endothelial cells sensitized with HVJ-liposome-DNA (concentration: 10 μg/ml) were similarly incubated, and the increased cells were counted to determine a cell growth rate (%). For control, the endothelial cells sensitized with HVJ-liposome-cont were also incubated, and the increased cells were counted to determine a cell growth rate (%). The results are shown in FIG. 2 (bar, n=6), wherein "DSF" designates the group of the endothelial cells sensitized with HVJ-liposome-cont, and "HGF" designates the group of the endothelial cells sensitized with HVJ-liposome-DNA (**: P<0.01 for DSF, #: P<0.05 for HGF, 100 ng/ml).

As is noted from the bar shown in FIG. 2, the results reveal that the cell growth rate of the HVJ-liposome-DNA-sensitized endothelial cells is markedly higher than that of the control group and significantly high even when compared to that of the exogenously added HGF.

Figure 3:
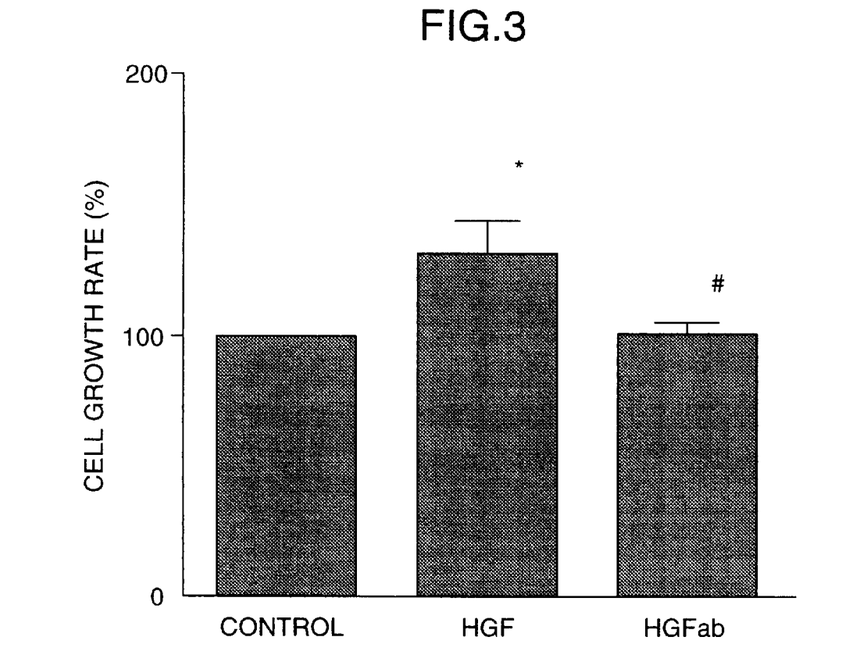
FIG. 3 shows a cell growth rate of endothelial cells sensitized with HVJ-liposome-DNA in the presence or absence of anti-HGF antibody in Test Example 2, wherein "control" represents a group of the HVJ-liposome-cont-sensitized endothelial cells incubated in the presence of IgG control; "HGF" represents a group of the HVJ-liposome-DNA-sensitized endothelial cells incubated in the presence of IgG control; and "HGFab" represents a group of the HVJ-liposome-DNA-sensitized endothelial cells incubated in the presence of a rabbit anti-human HGF antibody. The cell growth rate (%) is expressed in terms of relative % when the growth rate in the control group is made 100.

The aforesaid endothelial cells sensitized with HVJ-liposome-DNA were incubated in the presence or absence of a rabbit anti-human HGF antibody. The cells increased were counted to determine a cell growth rate. For control, the endothelial cells sensitized with HVJ-liposome-cont were incubated, and the cells increased were counted in a similar manner to determine a cell growth rate. The rabbit anti-human HGF antibody (10 μg/ml) was purified by the method as described in Jpn. J. Cancer Res., 83, 1262–1266 (1992). This antibody is capable of neutralizing the biological activity of 10 ng/ml in its concentration of 10 μg/ml. The anti-human HGF antibody is cross-reactive only with human HGF but not with rat HGF, whereas the anti-rat HGF antibody is cross-reactive only with rat HGF but not with human HGF. Normal rabbit serum IgG (10 μg/ml) was used for control.

The results are shown in FIG. 3 (n=6), wherein "control" designates the group of HVJ-liposome-cont-sensitized endothelial cells incubated in the presence of IgG control; "HGF" designates the group of HVJ-liposome-DNA-sensitized endothelial cells incubated in the presence of IgG control; and "HGFab" designates the group of HVJ-liposome-DNA-sensitized endothelial cells incubated in the presence of the rabbit anti-human HGF antibody. The cell growth rate (%) is expressed in terms of relative % when the growth rate in the control group is made 100 (*: P<0.01 for the control group, #: P<0.05 for HGF). As shown in FIG. 3, the growth of HVJ-liposome-DNA-sensitized endothelial cells was arrested in the presence of the anti-human HGF antibody, and the cell growth rate was thus substantially the same as that of the control group. These results clearly demonstrate that HGF is the growth factor of endothelial cells.

TEST EXAMPLE 3

Effects of the Supernatant of the Incubated HVJ-liposome-DNA-sensitized Rat VSMCs on Rat Coronary Endothelial Cells The supernatant from the incubated HVJ-liposome-DNA-sensitized rat VSMCs were added to the rat coronary endothelial cell culture system (cell count: $10^5$) during the stationary phase. After incubation was conducted for 3 days, the count of the endothelial cells increased was examined. For control, the supernatant of the incubated HVJ-liposome-cont-sensitized rat VSMCs were treated in the similar manner as described above, and the endothelial cells increased were counted as described above. The results are shown in FIG. 4 (n=6), wherein "control" indicates the group added with the supernatant from the incubated HVJ-liposome-cont-sensitized rat VSMCs, and "HGF" represents the group added with the supernatant of the incubated HVJ-liposome-DNA-sensitized rat VSMCs.

Figure 4:
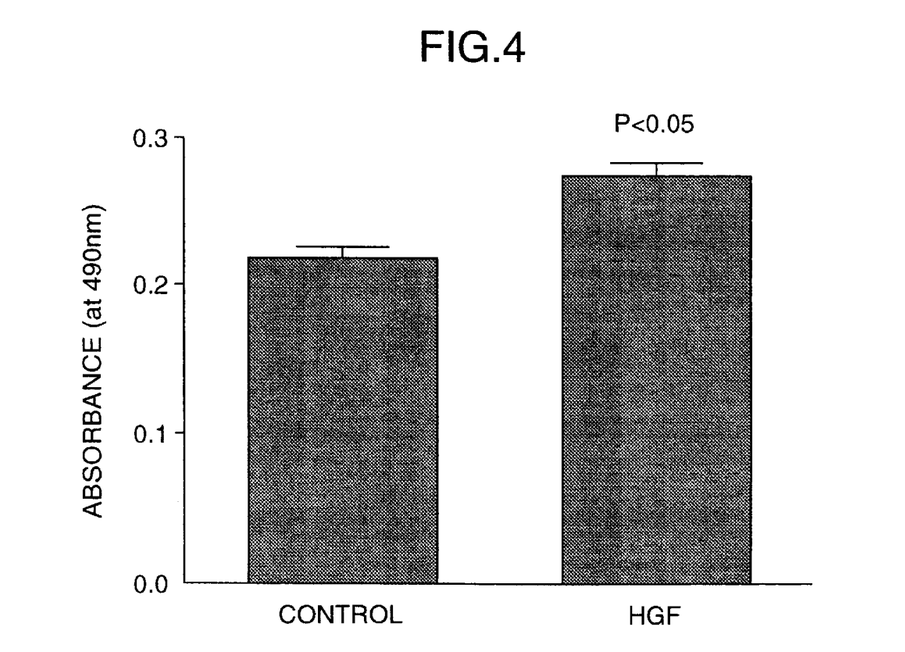
FIG. 4 is a graph showing the cell growth effect of the culture supernatant from the HVJ-liposome-DNA-sensitized rat vascular smooth muscle cells (hereinafter often abbreviated as VSMCs) on rat coronary endothelial cells in Test Example 3, wherein "control" designates a group added with the culture supernatant from the HVJ-liposome-cont-sensitized rat VSMCs, and "HGF" designates a group added with the culture supernatant from the HVJ-liposome-DNA-sensitized rat VSMCs.

As shown in FIG. 4, a significant increase in the count of endothelial cells was noted in the group added with the supernatant of the incubated HVJ-liposome-DNA-sensitized rat VSMCs.

Figure 5:
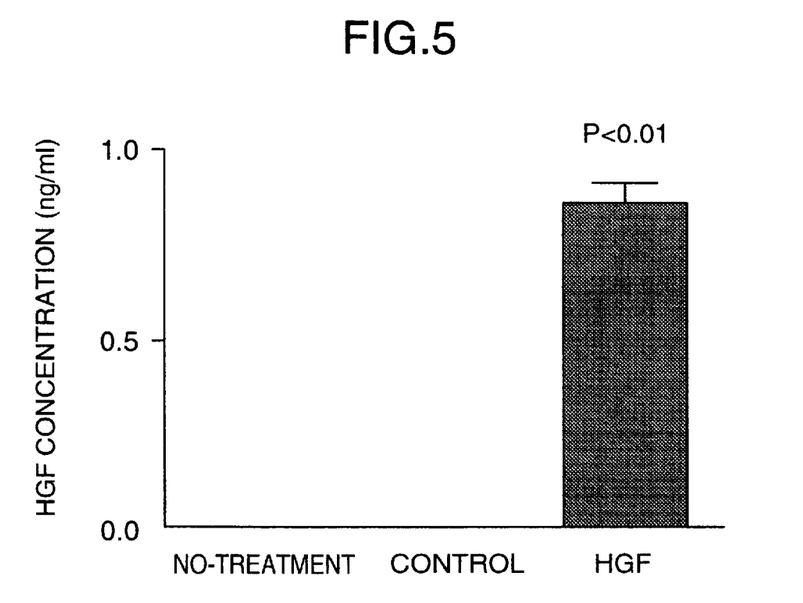
FIG. 5 is a graph showing the results in Test Example 3 in which the concentration of HGF in the supernatant from the incubated HVJ-liposome-DNA-sensitized rat VSMCs was determined using the anti-human HGF antibody. In the figure, "no-treatment" represents a group of the culture supernatant of non-sensitized VSMCs; "control" represents a group of the supernatant from the incubated HVJ-liposome-cont-sensitized rat VSMCs; and "HGF" represents a group of the supernatant from the incubated HVJ-liposome-DNA-sensitized rat VSMCs.
Figure 6:
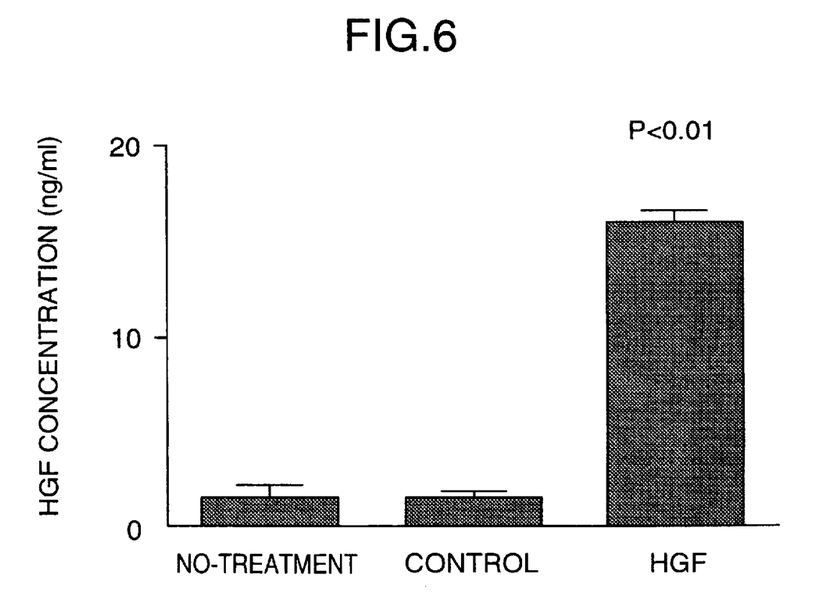
FIG. 6 is a graph showing the results in Test Example 3 in which the concentration of HGF in the supernatant from the incubated HVJ-liposome-DNA-sensitized rat VSMCs was determined using the anti-rat HGF antibody. In the figure, "no-treatment" represents a group of the culture supernatant of non-sensitized VSMCs; "control" designates a group of the supernatant from the incubated HVJ-liposome-cont-sensitized rat VSMCs; and "HGF" designates a group of the supernatant from the incubated HVJ-liposome-DNA-sensitized rat VSMCs.

The concentration of HGF in the culture supernatant of the rat VSMCs sensitized with HVJ-liposome-DNA or HVJ-liposome-cont as described above was assayed by ELISA using an anti-human HGF antibody and an anti-rat HGF antibody. The HGF concentration in the culture supernatant of non-sensitized VSMCs was also assayed (no-treatment group).

The results obtained using the anti-human HGF antibody and the anti-rat HGF antibody are shown in FIGS. 5 and 6, respectively (n=6 in both tests). In the figure, "control" designates the group of the supernatant from the incubated HVJ-liposome-cont-sensitized rat VSMCs; and "HGF" designates the group of the supernatant from the incubated HVJ-liposome-DNA-sensitized rat VSMCs.

As shown in FIG. 5, HGF was detected in the supernatant of the HVJ-liposome-DNA-sensitized rat VSMCs, and the HGF concentration was significantly higher than that of the control group.

FIG. 6 also reveals that rat HGF was further detected in the supernatant of the HVJ-liposome-DNA-sensitized rat VSMCs, and the HGF concentration was significantly higher than that of the control group.

As observed in FIGS. 5 and 6, no HGF was present in an amount detectable by ELISA, in both the supernatants of the intact group and the control group.

TEST EXAMPLE 4

Effects of the Supernatant from the Incubated HVJ-liposome-DNA-Sensitized Rat Coronary Endothelial Cells on Rat Coronary Endothelial Cells The supernatant of the incubated HVJ-liposome-DNA-sensitized rat coronary endothelial cells were added to the rat coronary endothelial cell culture system (cell count: $10^5$) during the stationary phase. After incubation for 3 days, the count of the increased endothelial cells was examined. For control, the endothelial cells were incubated in the similar manner, using the culture supernatant of the HVJ-liposome-cont-sensitized rat coronary endothelial cells, and the increased endothelial cells were counted. The results are shown in FIG. 7, wherein A, B and C represents, respectively, the group added with the culture supernatant of the HVJ-liposome-DNA-sensitized rat coronary endothelial cells (n=8), the group added with the culture supernatant of the HVJ-liposome-cont-sensitized rat coronary endothelial cells (n=8), and the no-treatment group (n=15).

Figure 7:
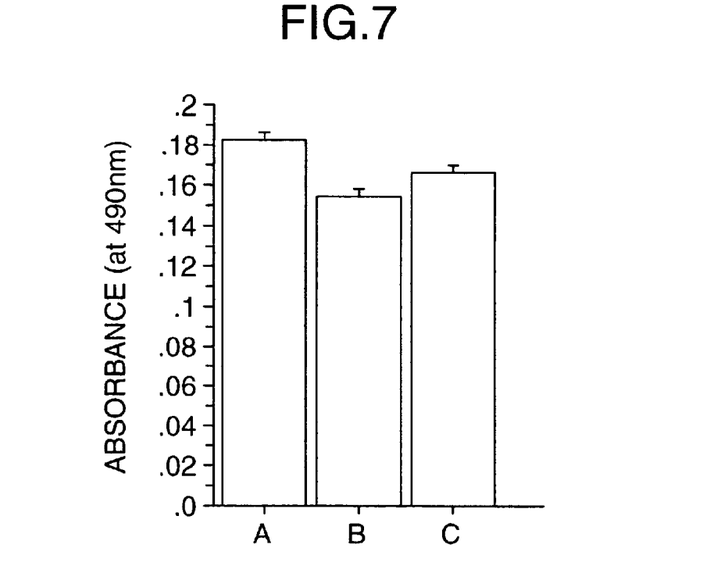
FIG. 7 is a graph showing the cell growth effect of the supernatant from the incubated HVJ-liposome-DNAsensitized rat coronary endothelial cells on rat coronary endothelial cells in Test Example 4, wherein A, B and C designate, respectively, a group added with the supernatant of the incubated HVJ-liposome-DNA-sensitized rat coronary endothelial cells, a group added with the supernatant of the incubated HVJ-liposome-cont-sensitized rat coronary endothelial cells, and a group of no-treatment animals.

As shown in FIG. 7, a significant increase in the count of endothelial cells was noted in the group added with the culture supernatant of the HVJ-liposome-DNA-sensitized rat coronary endothelial cells, whereas in the control group, the cell count was almost the same as that of the no-treatment group (control group: 0.117±0.002, group A: 0.148±0.03, P<0.01).

Figure 8:
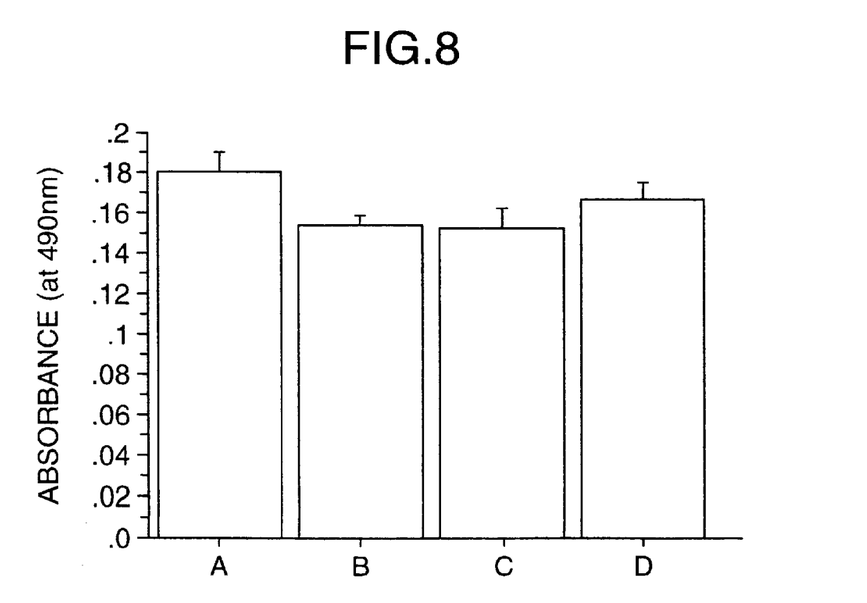
FIG. 8 shows the cell growth effect of HVJ-liposome-DNA-sensitized rat coronary endothelial cells on rat coronary endothelial cells in the presence of an anti-HGF antibody in Test Example 4. In the figure, A represents a group added with the supernatant from the incubated HVJ-liposome-DNA-sensitized rat coronary endothelial cells; B represents a group added with the supernatant from the incubated HVJ-liposome-cont-sensitized rat coronary endothelial cells; C represents a group added with the anti-HGF antibody to the supernatant from the incubated HVJ-liposome-DNA-sensitized rat coronary endothelial cells; and D represents a group added with the control antibody to the supernatant of the incubated HVJ-liposome-DNA-sensitized rat coronary endothelial cells.

Next, an anti-HGF antibody was added to the culture supernatant of the HVJ-liposome-DNA-sensitized rat coronary endothelial cells. The count of increased endothelial cells was examined as described above. The results are shown in FIG. 8 (n=8), wherein A represents the group added with the culture supernatant of the HVJ-liposome-DNA-sensitized rat coronary endothelial cells; B represents the group added with the culture supernatant of the HVJ-liposome-cont-sensitized rat coronary endothelial cells; C represents the group added with the anti-HGF antibody to the culture supernatant of the HVJ-liposome-DNA-sensitized rat coronary endothelial cells; and D represents the group added with a control antibody to the supernatant from the incubated HVJ-liposome-DNA-sensitized rat coronary endothelial cells.

As shown in FIG. 8, A and C, the cell growth promoting activity of the culture supernatant of the HVJ-liposome-DNA-sensitized rat coronary endothelial cells completely disappeared by adding the anti-HGF antibody thereto. The results reveal that the cell growth promoting activity of the culture supernatant of the HVJ-liposome-DNA-sensitized rat coronary endothelial cells is attributed to HGF.

TEST EXAMPLE 5

Effects of HVJ-liposome-DNA-sensitized Human VSMCs on Human Endothelial Cells

Figure 9:
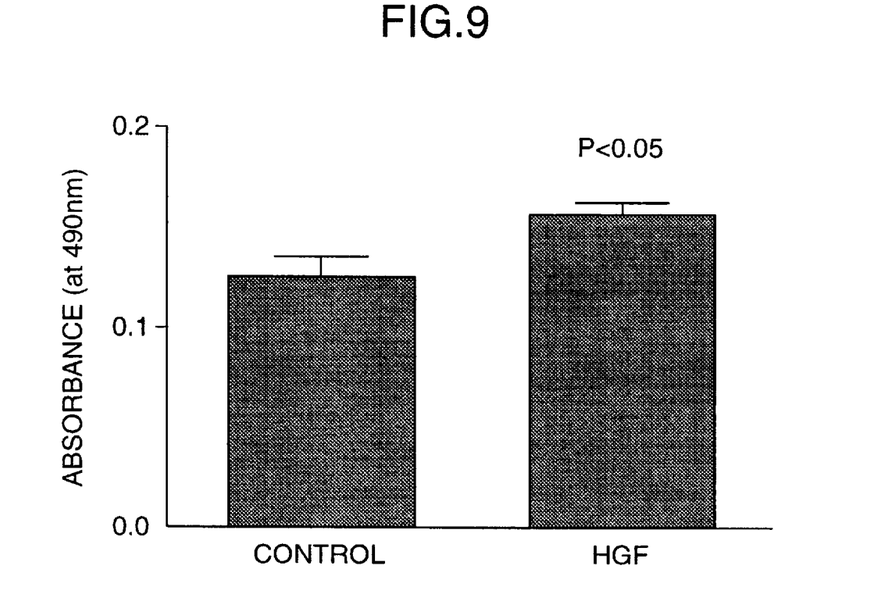
FIG. 9 is a drawing showing the cell growth of endothelial cells in Test Example 5 when HVJ-liposome-DNA-sensitized human VSMCs were co-incubated with non-sensitized human endothelial cells. In the figure, "control" represents a group co-incubated with HVJ-liposome-cont-sensitized VSMCs, and "HGF" represents a group of the supernatant from the incubated HVJ-liposome-DNA-sensitized VSMCs.

Human VSMCs were inoculated on a cell culture insert (manufactured by Coaster, pore diameter of 0.45 $\mu$m), which were then grown in DMEM medium supplemented with 10% bovine serum. On the other hand, human endothelial cells were inoculated on a 6-well plate and maintained in DMEM medium supplemented with 10% bovine serum. When VSMCs were proliferated to reach 80% confluence, VSMCs were incubated at 4° C. for 5 minutes and at 37° C. for 30 minutes together with HVJ-liposome-DNA (DNA content in the liposomes: 10 $\mu$g) or with HVJ-liposome-cont. After sensitization, the insert containing the sensitized VSMCs was added to each well containing human endothelial cells in the stationary phase. VSMCs and the endothelial cells were co-incubated for 3 days in DMEM medium supplemented with 0.5% bovine serum. Thereafter the cell count was determined with a WST-cell counter kit (manufactured by Wako Co.). The results are shown in FIG. 9 (n=6). In the figure, "control" represents the group co-incubated with the HVJ-liposome-cont-sensitized VSMCs, and "HGF" represents the group of the supernatant from the incubated HVJ-liposome-DNA-sensitized VSMCs.

The results shown in FIG. 9 reveal that human VSMCs sensitized with HVJ-liposome-DNA could significantly increase the growth of non-sensitized human endothelial cells in the stationary phase.

TEST EXAMPLE 6

Effects of the HVJ-liposome-DNA-sensitized Rat VSMCs on Rat Coronary Endothelial Cells The HVJ-liposome-DNA-sensitized rat VSMCs (cell count: $10^6$) were co-incubated for 3 days with rat coronary endothelial cells (cell count: $10^5$) in the stationary phase. Thereafter, the count of the increased endothelial cells was examined. For control, endothelial cells were co-incubated in the similar manner using the HVJ-liposome-cont-sensitized rat VSMCs, and the increased endothelial cells were counted. The results are shown in FIG. 10 (n=6), wherein "control" represents the rat VSMCs group sensitized with the HVJ-liposome-DNA, and "HGF" represents the rat VSMCs group sensitized with HVJ-liposome-cont.

Figure 10:
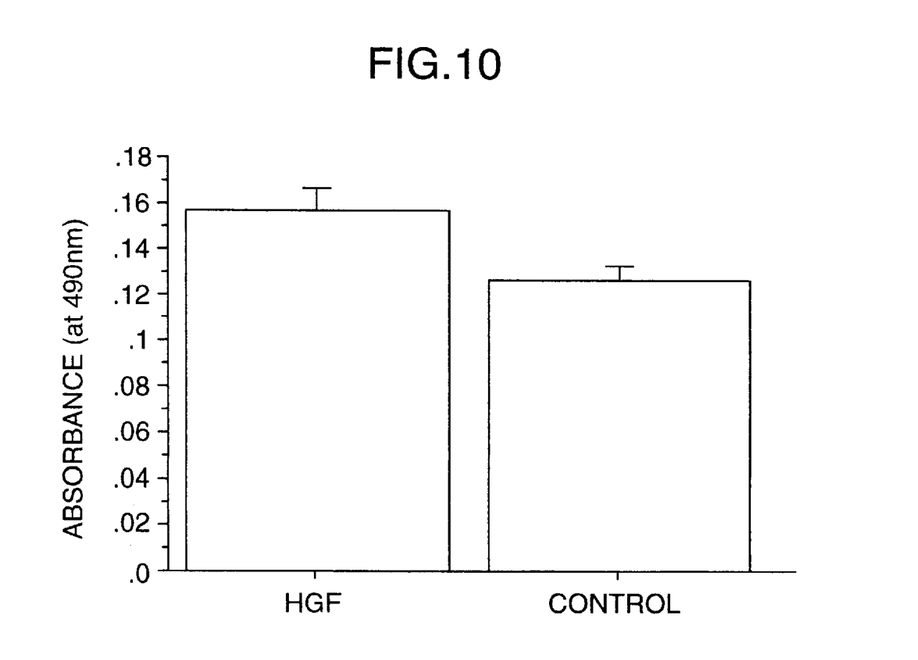
FIG. 10 indicates the cell growth of endothelial cells in Test Example 6 when HVJ-liposome-DNA-sensitized rat VSMCs were co-incubated with non-sensitized rat coronary endothelial cells. In the figure, "control" represents a group co-incubated with the HVJ-liposome-cont-sensitized VSMCs, and "HGF" represents a group of the culture supernatant of the HVJ-liposome-DNA-sensitized VSMCs.

As shown in FIG. 10, the growth of the endothelial cells was stimulated by HGF released from the HVJ-liposome-DNA-sensitized rat VSMCs, and the increased cell count was observed (control group: 0.126±0.006, HGF group: 0.156±0.01, P<0.05).

TEST EXAMPLE 7

Growth of Rat VSMCs Sensitized with HVJ-liposome-DNA

Rat VSMCs sensitized with HVJ-liposome-DNA and rat VSMCs sensitized with HVJ-liposome-cont were incubated, respectively, to make comparison of the increased cell count therebetween. Sensitization with HVJ-liposome-DNA did not affect cell growth at all. The results reveal that HGF has no cell growth promoting effect on VSMCs.

TEST EXAMPLE 8

Induction of Angiogenesis in Rat Heart Muscle Directly Injected with HVJ-liposome-DNA Rat heart muscle directly injected with HVJ-liposome-DNA, rat heart muscle directly injected with HVJ-liposome-cont and rat no-treatment heart muscle were stained with HE and Azan, respectively, and examined on a microscope to count the number of micro-vessels. The results are shown in FIG. 11, wherein "HGF" designates the number of microvessels in rat heart muscle directly injected with HVJ-liposome-DNA, and "control" designates the number of microvessels in rat heart muscle directly injected with HVJ-liposome-cont.

Figure 11:
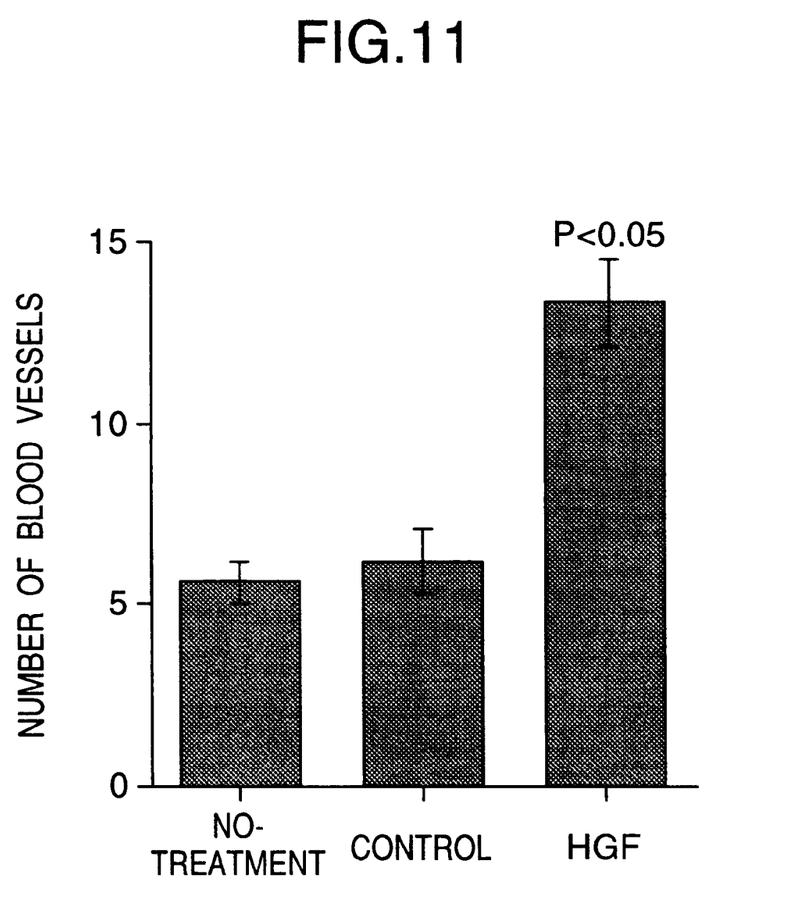
FIG. 11 shows an increase in the number of minute blood vessels in rat heart muscle directly injected with HVJ-liposome-DNA in Test Example 8, wherein "HGF" denotes the number of minute blood vessels in rat heart muscle directly injected with HVJ-liposome-DNA, and "control" denotes the number of minute blood vessels in rat heart muscle directly injected with HVJ-liposome-cont.

As is noted from FIG. 11, the number of minute blood vessels significantly increased in the rat heart muscle injected with HVJ-liposome-DNA, as compared to those of the rat heart muscle injected with HVJ-liposome-cont and the rat no-treatment heart muscle. These results reveal that HGF having the activity of growing endothelial cells exhibits an angiogenesis activity in vivo.

TEST EXAMPLE 9

Repair of Articular Cartilage by Directly Introducing HVJ-liposome-DNA into the Joint Ten weeks aged Fischer's rats were injured at the femoral intercondylaris through subcartilage using Kirschner's wires of 1.8 mm in diameter. One week after the operation, the HVJ-liposome-DNA (100 µl/knee) prepared in Example 1 was introduced directly into the joint. For control, the HVJ-liposome-cont prepared in Comparative Example 1 and HVJ-liposome-DNA (TGF-β) prepared in Comparative Example 2 were administered directly into the joint in the same amount. Rats were sacrificed 1, 3 and 4 weeks after introduction of these genes, etc. and the repaired sites were histologically observed.

Figure 12:
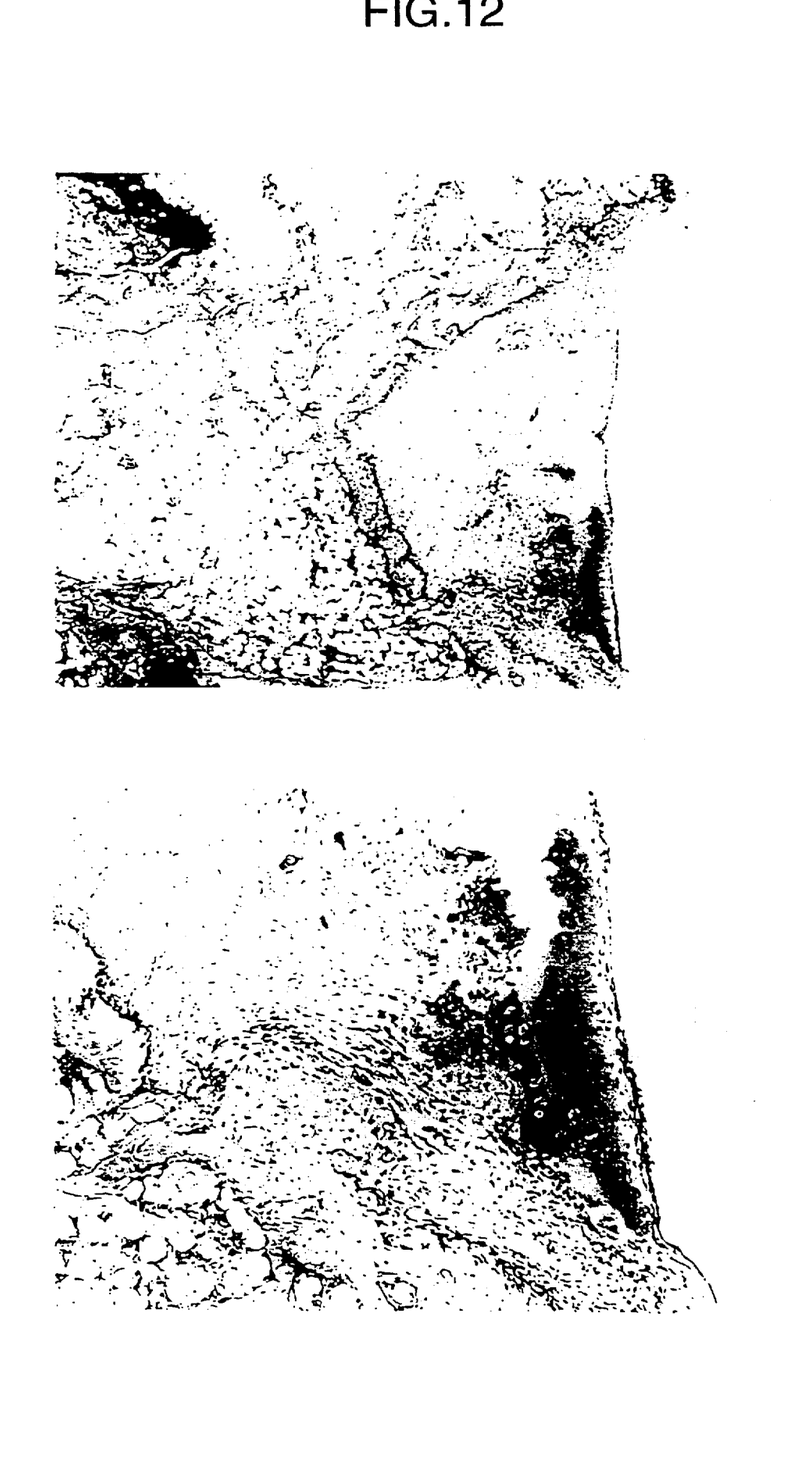
FIG. 12 is a drawing showing that 3 weeks after administration of HVJ-liposome-DNA into the joint, development of cartilage-like cells was noted in Test Example 9, in which the synthesis of Toluidine Blue-stained proteoglycan was observed.
Figure 13:
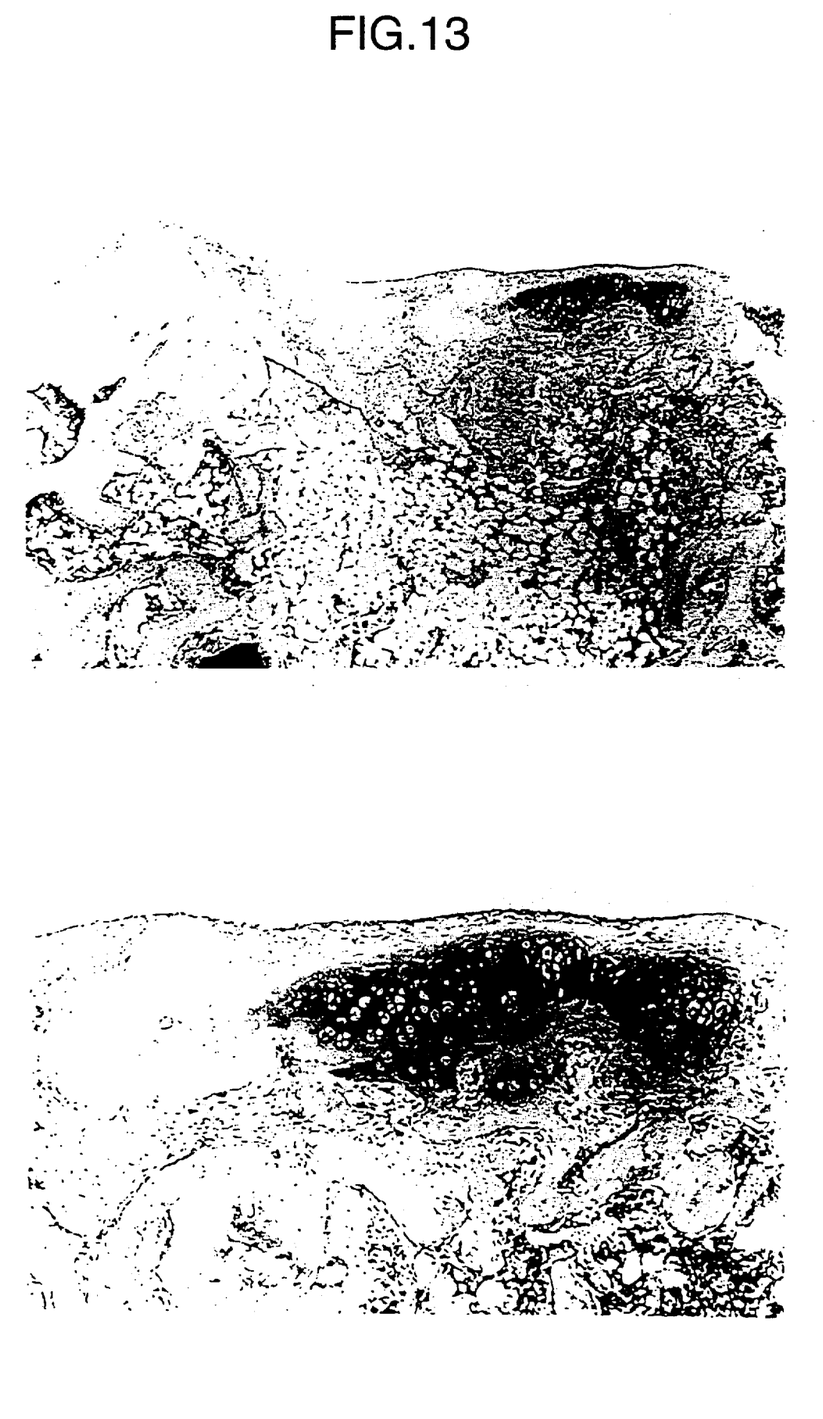
FIG. 13 is a drawing showing that 4 weeks after administration of HVJ-liposome-DNA into the joint, development of cartilage-like cells was noted in Test Example 9, in which the synthesis of Toluidine Blue-stained proteoglycan was observed.

As shown in FIG. 12, the results indicate that the synthesis of proteoglycan stained with Toluidine Blue was observed 3 weeks after administration of the HVJ-liposome-DNA into the joint, displaying the development of cartilage-like cells. Furthermore, as shown in FIG. 13, 4 weeks after administration of the HVJ-liposome-DNA into the joint, there was observed a tendency to further extend the area of developing cartilage-like cells, in which the synthesis of proteoglycan was recognized.

Figure 14:
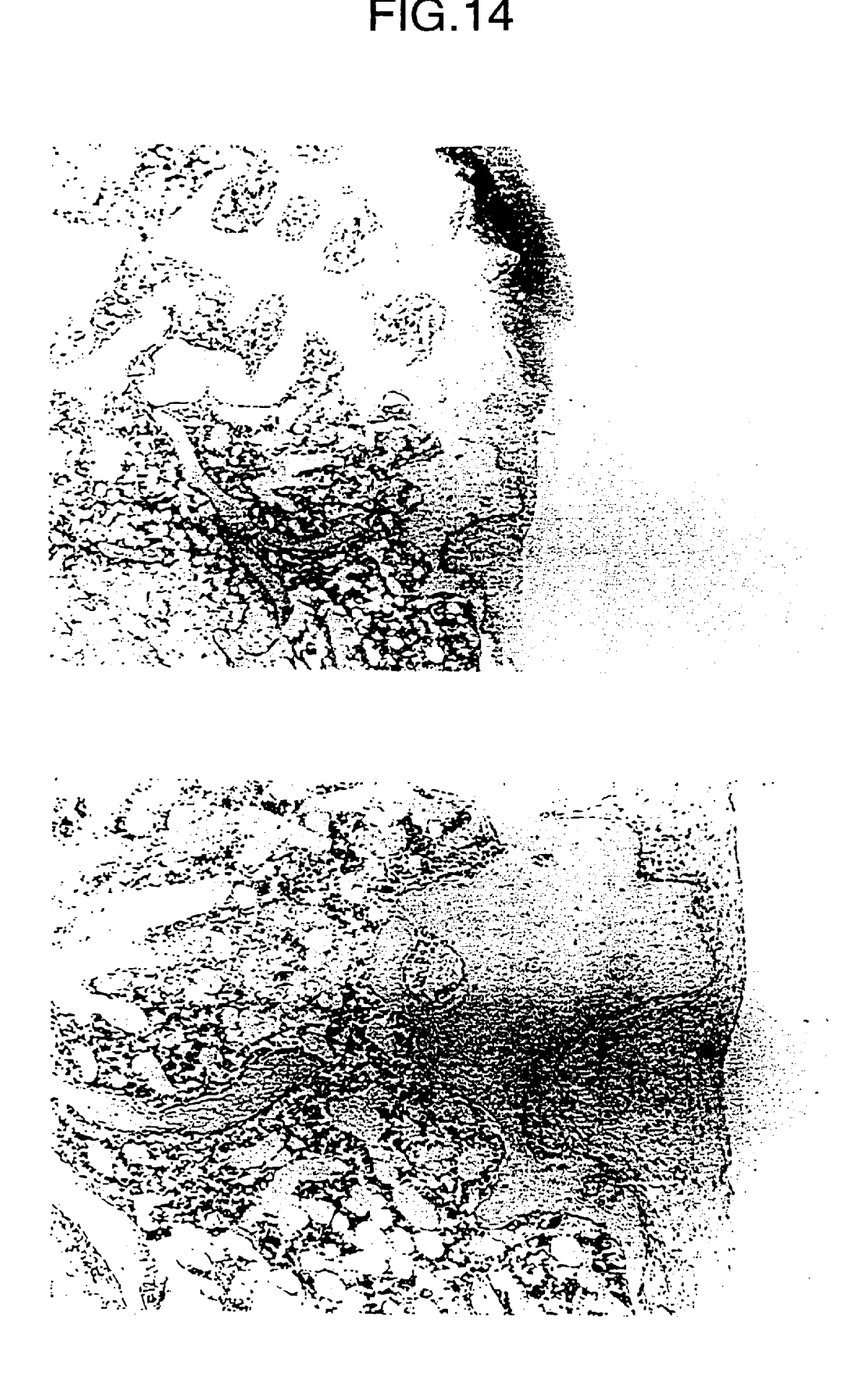
FIG. 14 is a drawing showing that even 4 weeks after administration of HVJ-liposome-DNA (TGF-$\beta$) prepared in Comparative Example 2 into the joint, such development of cartilage-like cells as observing Toluidine Blue-stained proteoglycan synthesis was not noted in Test Example 9.
Figure 15:
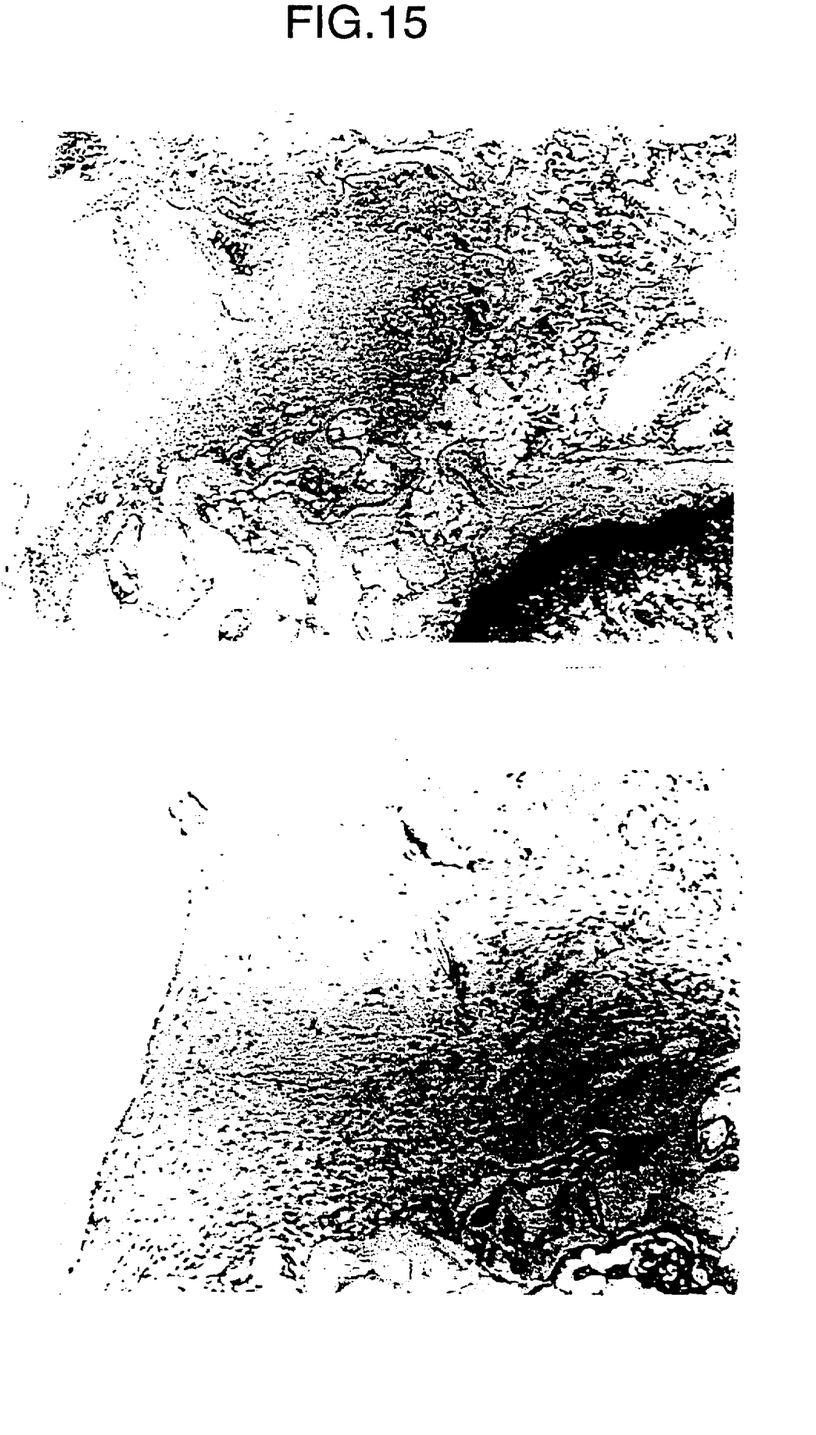
FIG. 15 is a drawing showing that even 4 weeks after administration of HVJ-liposome-cont prepared in Comparative Example 1 into the joint, no such development of cartilage-like cells as observing Toluidine Blue-stained proteoglycan synthesis was noted in Test Example 9.

As shown in FIG. 14, where the HVJ-liposome-DNA (TGF-β) prepared in Comparative Example 2 was injected into the joint, development of such cartilage-like cells was not observed even 4 weeks after the administration. Furthermore, as shown in FIG. 15, where the HVJ-liposome-cont prepared in Comparative Example 1 was injected into the joint, development of such cartilage-like cells was not observed even 4 weeks after the administration.

INDUSTRIAL APPLICABILITY

The medicament of the present invention provides persistent therapeutic effects, as compared to HGF itself. Moreover, the medicament of the present invention may be topically applied to the target organs so that the effects can be selectively exhibited, resulting in minimizing the side effects of HGF.

What is claimed is:

1. A method for treating a disease in a subject for which HGF is effective, comprising administering intramuscularly to the subject an expression vector containing a HGF gene in a therapeutically effective amount.

2. The method of claim 1, wherein said expression vector is selected from a viral expression vector containing a HGF gene and a non-viral expression vector containing a HGF gene.

3. The method of claim 1, wherein said subject has an arterial disease.

4. The method of claim 2, wherein said non-viral expression vector is encapsulated in a liposome, the membrane of which may be further fused to attenuated Sendai virus particles.

5. A method for accelerating the growth of vascular endothelial cells in a desired target tissue in a subject without accelerating the growth of vascular smooth muscle cells, comprising administering intramuscularly to the subject an expression vector containing a HGF gene in a therapeutically effective amount.

6. The method of claim 5, wherein said expression vector is a non-viral expression vector encapsulated in a liposome, the membrane of which may be further fused to attenuated Sendai virus particles.

* * * * *

UNITED STATES PATENT AND TRADEMARK OFFICE
CERTIFICATE OF CORRECTION

PATENT NO.      : 6,248,722 B1                                                      Page 1 of 1
DATED           : June 19, 2001
INVENTOR(S)     : Ryuichi Morishita et al.

It is certified that error appears in the above-identified patent and that said Letters Patent is hereby corrected as shown below:

<u>Title page,</u>
Item [73], please change "Sumitomo Pharmaceuticals Company, Limited, Osaka (JP)" to -- [73] Assignee: MedGene Bioscience, Inc., Osaka (JP) --

Signed and Sealed this

Twenty-seventh Day of May, 2003

JAMES E. ROGAN
*Director of the United States Patent and Trademark Office*